(12) United States Patent
Thapliyal (10) Patent No.: US 11,992,237 B2
(45) Date of Patent: May 28, 2024

(54) STEERABLE ABLATION CATHETER

(71) Applicant: AneuMed, Inc., Los Altos, CA (US)

(72) Inventor: Hira V Thapliyal, Los Altos, CA (US)

(73) Assignee: AneuMed, Inc., Los Altos, CA (US)

(*) Notice: Subject to any disclaimer, the term of this patent is extended or adjusted under 35 U.S.C. 154(b) by 286 days.

(21) Appl. No.: 17/125,508

(22) Filed: Dec. 17, 2020

(65) Prior Publication Data

US 2021/0186551 A1 Jun. 24, 2021

Related U.S. Application Data

(60) Provisional application No. 62/950,801, filed on Dec. 19, 2019.

(51) Int. Cl.
*A61B 17/32* (2006.01)
*A61B 17/00* (2006.01)
*A61B 17/22* (2006.01)
*A61B 90/00* (2016.01)
*A61N 1/05* (2006.01)

(52) U.S. Cl.
CPC .... *A61B 17/320068* (2013.01); *A61B 90/361* (2016.02); *A61N 1/0565* (2013.01); *A61B 2017/00243* (2013.01); *A61B 2017/00327* (2013.01); *A61B 2017/22051* (2013.01); *A61B 2017/320069* (2017.08); *A61B 2090/3614* (2016.02)

(58) Field of Classification Search
CPC ........... A61B 17/320068; A61B 2017/320069; A61B 2017/32007; A61B 2017/320071; A61B 2017/320072; A61B 2017/320073
See application file for complete search history.

(56) References Cited

U.S. PATENT DOCUMENTS

| | | |
|---|---|---|
| 2004/0176757 A1 | 9/2004 | Sinelnikov et al. |
| 2007/0219546 A1 | 9/2007 | Mody et al. |
| 2009/0030412 A1 | 1/2009 | Willis et al. |
| 2010/0049099 A1 | 2/2010 | Thapliyal et al. |
| 2015/0018725 A1 | 1/2015 | Sommer |
| 2016/0175041 A1 | 6/2016 | Govari et al. |
| 2017/0189106 A1 | 7/2017 | Schuler et al. |
| 2018/0368927 A1 | 12/2018 | Lyons et al. |

OTHER PUBLICATIONS

"International Application Serial No. PCT/US2020/065676, International Preliminary Report on Patentability dated Jun. 30, 2022", 10 pgs.
"International Application Serial No. PCT/US2020/065676, International Search Report dated Apr. 5, 2021", 3 pgs.
"International Application Serial No. PCT/US2020/065676, Written Opinion dated Apr. 5, 0221", 8 pgs.

*Primary Examiner* — Ashley L Fishback
(74) *Attorney, Agent, or Firm* — Schwegman, Lundberg & Woessner, P.A.

(57) ABSTRACT

A system for ablating target tissue includes an elongate anchor shaft, a radially expandable member coupled to the elongate anchor shaft, and an elongate ablation shaft. The radially expandable member has an expanded configuration for engagement with the target tissue to facilitate anchoring. The elongate ablation shaft may be slidably disposed in the elongate anchor shaft, and the distal portion of the elongate ablation shaft is steerable. An energy source is coupled to the elongate ablation shaft and is configured to deliver energy to the target tissue and ablate the target tissue. Actuation of the elongate ablation shaft directs the energy to the target tissue to form a desired ablation path in the target tissue.

23 Claims, 9 Drawing Sheets

STEERABLE ABLATION CATHETER

CLAIM OF PRIORITY

The present application is a non-provisional of, and claims the benefit of U.S. Provisional Patent Application No. 62/950,801 filed Dec. 19, 2019; the entire contents of which are incorporated herein by reference.

BACKGROUND

The condition of atrial fibrillation is characterized by the abnormal (usually very rapid) beating of the left atrium of the heart which is out of synchronization with the normal synchronous movement ("normal sinus rhythm") of the heart muscle. In normal sinus rhythm, the electrical impulses originate in the sino-atrial node ("SA node") which resides in the right atrium. The abnormal beating of the atrial heart muscle is known as fibrillation and is caused by electrical impulses originating instead in the pulmonary veins (also referred to herein as "PV").

There are pharmacological treatments for this condition with varying degrees of success. In addition, there are surgical interventions aimed at removing the aberrant electrical pathways from the pulmonary veins to the left atrium ("LA") such as the Cox-Maze III Procedure. Other minimally invasive procedures are also under development.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
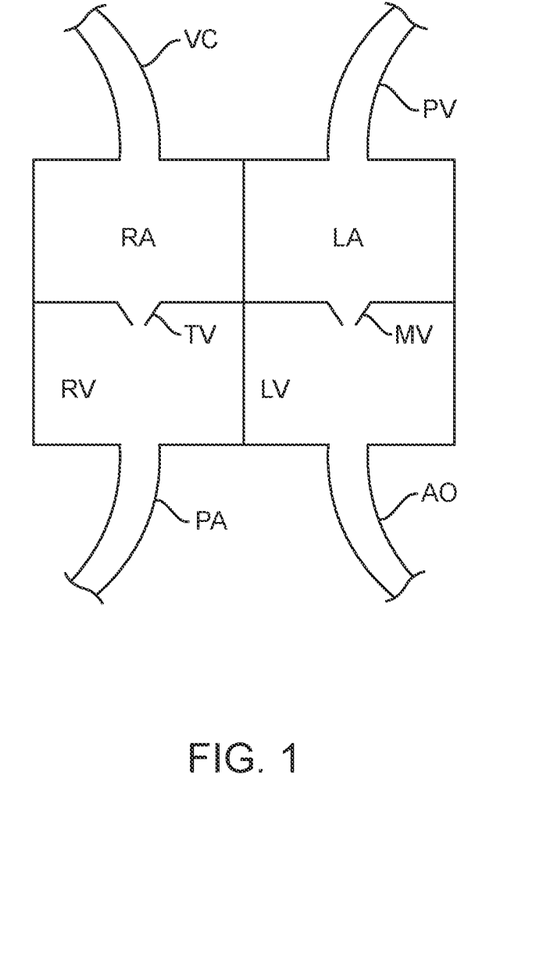
FIG. 1 illustrates basic human heart anatomy.

FIG. 1 illustrates basic human heart anatomy including the four chambers of the heart: right atrium RA, right ventricle RV, left atrium LA and left ventricle LV. The right atrium receives oxygen depleted blood returning from the body via the vena cava, VC which is then pumped into the right ventricle RV. A one-way check valve, the tricuspid valve TV prevents blood from back flowing into the right atrium. Blood is then pumped out of the right ventricle into the lungs via the pulmonary artery PA. Another one-way check valve, the pulmonary valve (not shown) prevents blood from back flowing into the right ventricle. Once blood flows into the lungs, it is oxygenated and then returned to the left atrium LA via the pulmonary veins PV. FIG. 1 only shows a single pulmonary vein for convenience, but often there are four pulmonary veins, two right pulmonary veins and two left pulmonary veins. The now oxygenated blood flows from the left atrium into the left ventricle via the mitral valve MV which prevents back flow from the left ventricle to the left atrium. The left ventricle then pumps the blood out the aorta AO (aortic valve not shown for convenience) and then the oxygenated blood is directed to the body.

Figure 2:
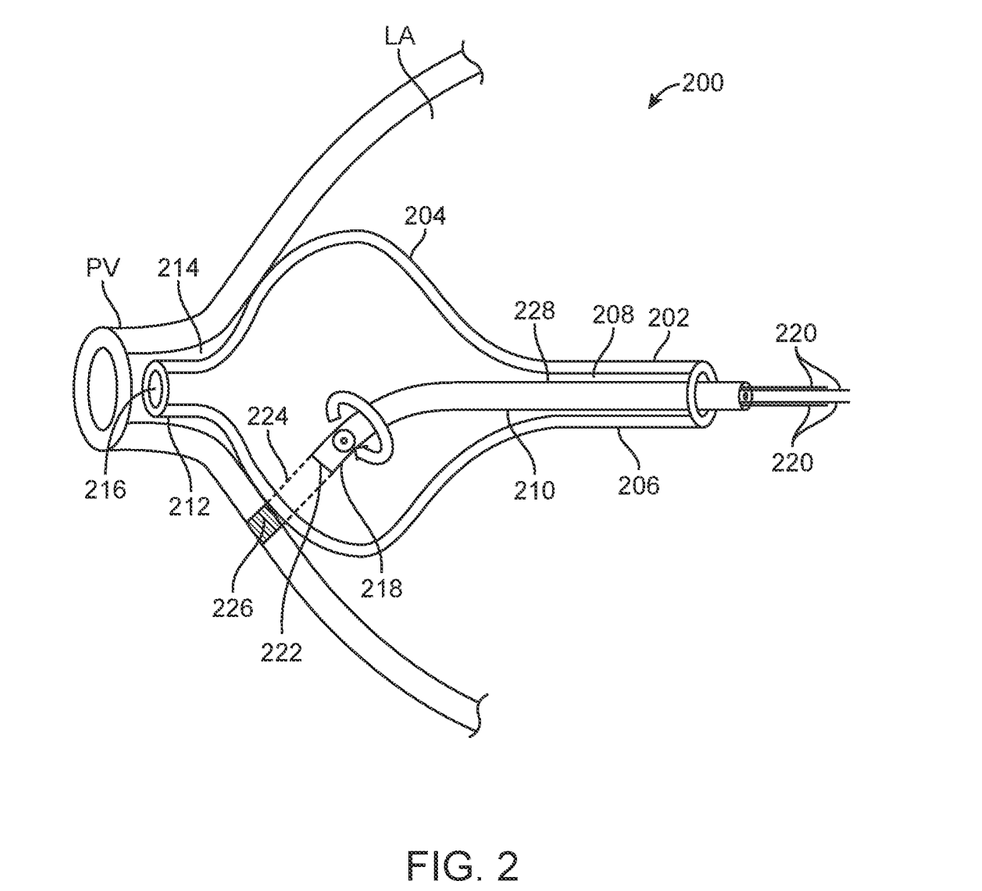
FIG. 2 illustrates an example of an ablation system.

FIG. 2 illustrates an example of an ablation system 200 that may be used to ablate tissue in the heart such as in the pulmonary veins PV in the left atrium LA as a treatment for atrial fibrillation. Other tissue in other regions of the heart or the body may also be ablated as a treatment for other cardiac arrhythmias such as ventricular tachycardia or as a treatment for other medical conditions and therefore the examples disclosed herein are not limited to treatment of atrial fibrillation.

In FIG. 2, the ablation system 200 includes an anchor catheter 202 having a radially expandable member 204 such as a balloon which is coupled to a balloon tube, also referred to as an elongate anchor shaft 206. The balloon tube 206 may have a central lumen 208 for receiving the ablation catheter 210, and may have another inflation lumen (not shown) for inflating the radially expandable member 204. The radially expandable member 204 is coupled to the distal portion of the balloon tube 206. The distal portion of the radially expandable member may include a nipple 212 that is sized and shaped to fit into the ostium 214 of the target pulmonary vein PV and that is fluidly coupled with the balloon. Additionally, the distal end of the nipple may include a bleeder hole 216 to allows excess fluid to exit therefrom or to allow other instruments to exit therefrom as will be discussed later in this specification. The bleeder hole 216 may be sufficiently small so that any fluids leaking therefrom do not have a negative effect, or a small valve such as a duckbill valve may be disposed in the bleeder hole to minimize or prevent fluid leakage and thus the balloon does not collapse. The anchor catheter not only helps anchor the device to the pulmonary vein but also helps center the device relative to the pulmonary vein.

An ablation catheter 210 with an elongate shaft 228 may be disposed in the central lumen 208 of the balloon tube 206 and the distal portion 218 of the ablation catheter may be disposed within the radially expandable member 204. One or more pull wires 220 may be disposed in lumens in the side wall of the ablation catheter 210 and their distal ends may be coupled to a distal portion of the ablation catheter (best illustrated in FIGS. 3, 3A and 3B). In this example, four pull wires 220 are disposed in the ablation catheter wall and they are spaced approximately 90 degrees apart from one another circumferentially. The ends of the pull wires may be coupled to the ablation catheter at the same axial location along the longitudinal axis, or they may be axially offset from one another to allow formation of a compound curve. Often, the pull wires may cooperate with one another in pairs so that when tension is applied to one pull wire, the pull wire 180 degrees opposite of that wire is in a relaxed configuration thereby steering the distal end of the ablation catheter in one direction by bending the tip. When desired, tension may be released on the initial pull wire and applied to the opposite pull wire to steer the distal end of the ablation catheter in an opposite direction. By combining this motion with the other pull wires, the distal tip of the ablation catheter may be steered in a circular or substantially circular motion around the ostium of a pulmonary vein, or any steering pattern may be used including but not limited to elliptical, square, rectangular, triangular, polygonal, or any other closed or open loop geometry, as indicated by the arrow in FIG. 2. The pull wires may be actuated manually, or they may be coupled to one or more actuators such as rotating knobs, levers, sliders, etc. on a handle that may be coupled to proximal end of the ablation catheter. Actuators and handles are not illustrated.

An energy source 222 such as an ultrasound transducer may be coupled to the distal end or near the distal end of the elongate shaft 228 of the ablation catheter 210 and the ultrasound transducer provides a beam of energy 224 exiting distally from the ultrasound transducer. In some examples, the energy is a collimated beam of low intensity ultrasound having enough power to create a transmural lesion 226 in the target tissue. Therefore, power may be 10 Watts or less, 5 Watts or less, 3 Watts or less, 2 Watts or less, or 1 Watt or less. A header disposed between the ultrasound transducer and the distal end of the ablation catheter (best seen in FIGS. 3 and 3A) may be used to join the ultrasound transducer to the ablation catheter and is discussed in more detail below. Wires may be coupled to the ultrasound transducer and those wires may run through lumens in the wall of the ablation catheter and extend proximally to a power source that drives the ultrasound transducer. This is also best illustrated in FIGS. 3 and 3A below.

In use the ablation catheter 210 may rotate around its longitudinal axis in combination with the tip steering actuated by the pull wires in order to direct ultrasound energy to any desired target tissue. Also the ablation catheter may be advanced distally and retracted proximally relative to the balloon to bring the energy source closer to or further away from the target tissue. Or, only tip steering by actuation of pull wires maybe used and rotation of the ablation catheter about its longitudinal axis may not be used with or without distal advancement and proximal retraction of the ablation catheter. In any example, the energy may be directed to form a closed ring or loop around the ostium of one or more pulmonary veins. The closed ring creates a conduction block thereby preventing aberrant electrical signals from propagating out of the pulmonary vein into the rest of the heart thereby eliminating or reducing atrial fibrillation. Examples of closed loop ablation paths which may be created using any of the examples of ablation devices or systems disclosed herein are illustrated later in this specification.

The expandable member 204 may be a balloon in any example and may be inflated with any fluid such as a gas or a liquid such as saline or contrast media. Contrast material may be mixed in with the saline so the inflated balloon is more easily visualized under fluoroscopy. If the balloon is over pressurized, the excess fluid may be vented through the bleeder hole 216 which may be a small hole in the distal portion of the expandable member or in the distal portion of the nipple.

Figure 3:
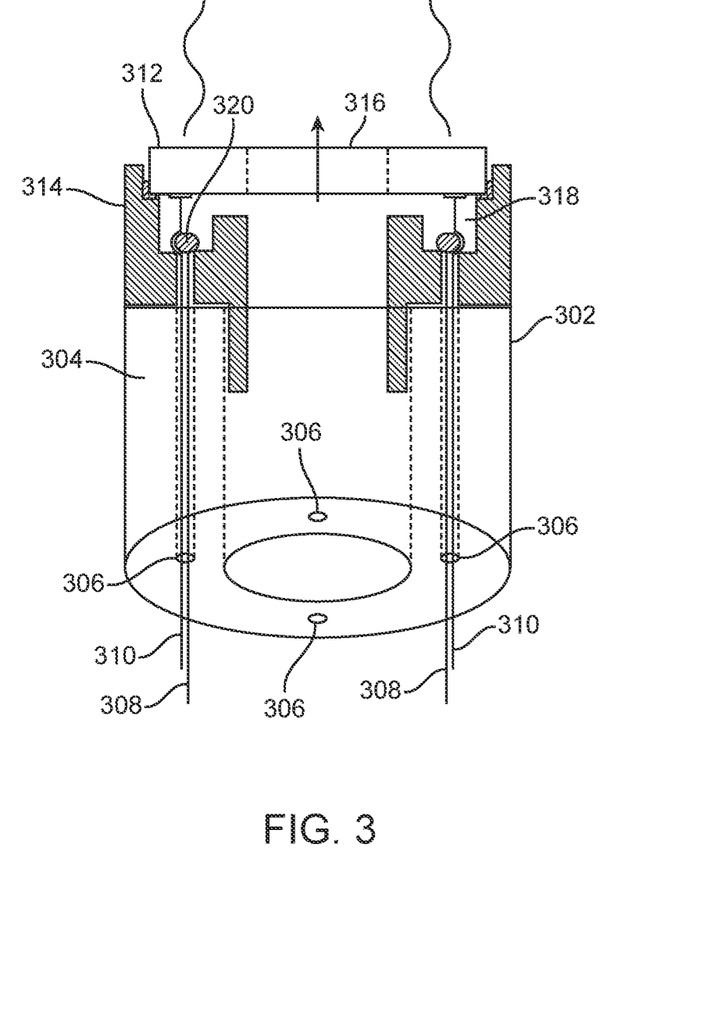
FIG. 3 shows a distal end of the ablation system in FIG. 2.

FIG. 3 highlights some of the optional features of the distal portion 302 of the ablation catheter shaft 228 (best seen in FIG. 2) that may be used in any example of an ablation system disclosed herein. The wall 304 of the ablation catheter shaft may have one or more lumens 306 which are used to house the pull wires 308 and/or the electrical wires 310 coupled to the ultrasound transducer 312. The pull wires 308 may be individually disposed in separate lumens or a lumen may be used to house one or more pull wires 308 and one or more electrical wires 310. Or the electrical wires 310 may be housed individually in separate lumens in the wall of the ablation catheter. A header 314 may be coupled to the distal end of the ablation catheter shaft and provides a seat on which the ultrasound transducer 312 may be coupled to such as with adhesive. In any example, the pull wires 308 may also be coupled to the header 314 instead of coupling the pull wires to the catheter shaft. The ultrasound transducer 312 may be a circular disc with a hole 316 through the center to allow fluid to flow past the transducer for cooling purposes as indicated by the linear arrow. Additionally, the header may include recesses 318 for receiving the pull wires and allowing them to be secured to the header. In this example, the pull wires include an enlarged head 320 such as a spherical ball coupled to the distal end of the pull wire and the size of the enlarged head is greater than the lumen size thereby preventing the pull wire from releasing from the header. The transducer 312 may be a piezoelectric material such as those known in the art and the transducer may emit a low intensity collimated beam of ultrasound. The beam may exit orthogonally relative to the ultrasound transducer and in a distal direction as indicated by the undulating arrows. The aperture may also allow other instruments to exit the distal end of the ablation shaft as will be discussed later.

Figures 3A, 3B:
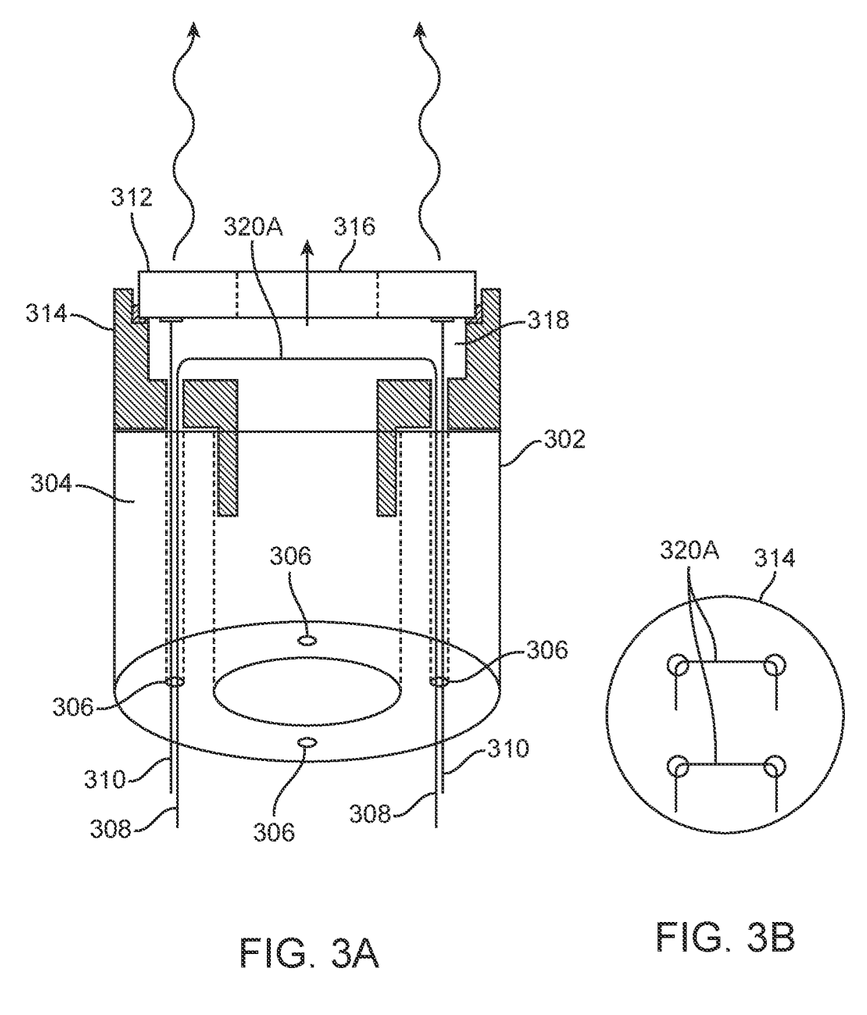
FIG. 3A shows another example of a distal end of the ablation system in FIG. 2.
FIG. 3B shows an example of pull wires in the distal end of the ablation system shown in FIG. 3A.

In another example, FIG. 3A highlights some of the optional features of the distal portion 302 of the ablation catheter shaft 228 (best seen in FIG. 2) that may be used in any example of an ablation system disclosed herein. FIG. 3A is similar to FIG. 3 with the major difference being how the pull wires interact with the distal portion of the ablation catheter.

The wall 304 of the ablation catheter shaft may have one or more lumens 306 which are used to house the pull wires 308 and/or the electrical wires 310 coupled to the ultrasound transducer 312. The pull wires 308 may be individually disposed in separate lumens or a lumen may be used to house one or more pull wires 308 and one or more electrical wires 310. Or the electrical wires 310 may be housed individually in separate lumens in the wall of the ablation catheter. A header 314 may be coupled to the distal end of the ablation catheter shaft and provides a seat on which the ultrasound transducer 312 may be coupled to, such as with adhesive. In this example, rather than discrete pairs of pull wires to, a single pull wire is used with one free end of the pull wire actuatable at that end, and the pull wire then runs along the ablation catheter distally into the header, across the header and then runs proximally back towards the proximal end of the ablation catheter where the second free end of the pull wire is also actuatable. The first and second ends maybe manually controlled and manipulated or they may be coupled to an actuator such as a slider, rotating know, or other actuation mechanism to apply tension to one side of the pull wire while the other side relaxes, and vice versa. Thus, in this example, there could be one, two, three, four, or more pull wires that allow formation of a curve in the distal tip. For example, if two pull wires are used, there would be four free ends but only two continuous pull wires.

The ultrasound transducer 312 may be a circular disc with a hole 316 through the center to allow fluid to flow past the transducer for cooling purposes as indicated by the linear arrow. Additionally, the header may include recesses 318 for receiving the pull wires and allowing them to extend across the header and return back proximally alongside the ablation catheter shaft. The transducer 312 may be a piezoelectric material such as those known in the art and the transducer may emit a low intensity collimated beam of ultrasound. The beam may exit orthogonally relative to the ultrasound transducer and in a distal direction as indicated by the undulating arrows. The aperture may also allow other instruments to exit the distal end of the ablation shaft as will be discussed later.

FIG. 3B shows an example of two pull wires used in the example of FIG. 3A where each pull wire extends out of one lumen, has a short segment 320a that runs across the header 314 and then passes back down into another lumen. The pull wires here are shown extending parallel across the header, but they may be routed diagonally or in any direction across the header as required in order to allow steering of the distal tip of the ablation catheter.

Figure 4:
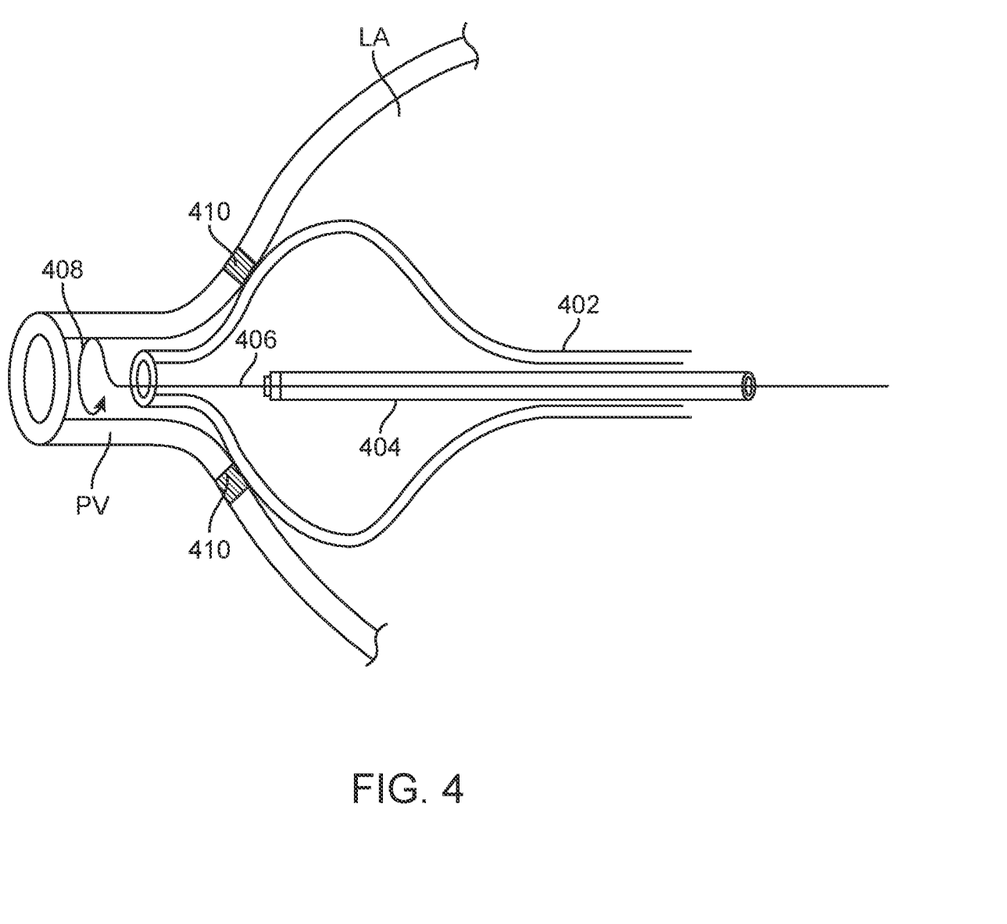
FIG. 4 shows a pacing lead used in conjunction with the ablation system of FIG. 2.

FIG. 4 illustrates other optional features which may be included in any example of ablation system disclosed herein, including a pacing lead 406. Once the desired lesion 410 has been formed around one or more pulmonary veins PV or around the ostium to one or more pulmonary veins, a physician may desire to verify that the aberrant electrical signals originating in the pulmonary vein cannot propagate out of the pulmonary vein past the lesion into the remainder of the heart. An optional pacing lead 406 maybe advanced through a lumen in the ablation catheter 404, through the expandable member 402 and out the bleeder hole into the pulmonary vein. The ablation catheter may be retraced proximally so that it does not extend distally past the bleeder hole and the distal portion of the ablation catheter may be disposed under the expandable member, here a balloon. The bleeder hole may also have a valve (e.g. a duckbill valve) to prevent excessive leaking of fluid out of the balloon. The pacing lead 406 may be a self-expanding material and may form a loop 408 at the distal end which expands into engagement with the walls of the pulmonary vein. The pacing lead acts as an electrode and may be energized from an energy source outside the patient. If the transmural lesion 410 is effective then the pacing signal from the pacing electrode cannot conduct past the lesion 410 and affect heart rhythm. However, if the lesion is not effective then the physician will observe a change in heart rhythm based on the pacing lead signal detected by an electrocardiogram or other method, and then the physician may attempt to continue ablating the tissue to prevent conduction across the lesion. Once the lesion has been determined to be adequate, the pacing lead maybe removed from the patient. The pacing lead may be slidably advanced and retracted into and out of the pulmonary vein via the ablation catheter and the expandable member catheter which acts as an anchor and helps center the catheters.

Figure 5:
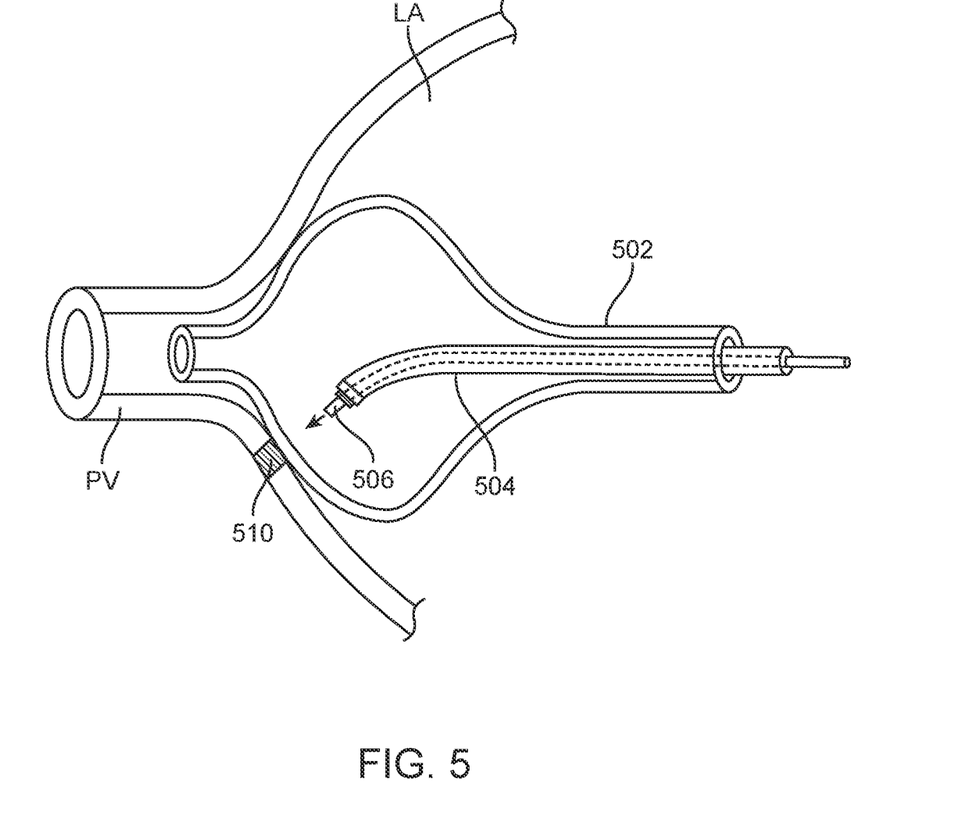
FIG. 5 shows an imaging element used in conjunction with the ablation system of FIG. 2.

FIG. 5 shows another optional feature which may be used in any example of ablation system disclosed herein, and includes an imaging element 506. Here, the imaging element 506 is a fiber optic element disposed through a lumen in the ablation catheter 504 which may be any of the ablation catheters disclosed herein. The imaging element 506 is disposed past the ultrasound transducer into the balloon of the expandable member catheter 502. The ablation catheter 504 may be retracted proximally so it does not extend past the bleeder hole in the balloon. Thus, the fiber optic tip may be steered along with steering of the ablation catheter distal end using any steering mechanism such as the pull wires disclosed herein. As the pull wires are actuated to steer the ablation catheter 504, the fiber optic element will move with the ablation catheter. The fiber optic element will allow the target treatment area to be illuminated with light and an image of the treatment area including the lesion 510 can be viewed on a monitor outside the patient. Thus, the physician can view the lesion and verify that an appropriate lesion has been formed around the pulmonary vein or around the pulmonary veins in the left atrium LA. The fiber optic is disposed in the expandable member and is capable of providing an image through the inflation fluid in the balloon and through the balloon material. Once the lesion has been verified by optically viewing the lesion, the fiber optic may be removed from the ablation catheter.

FIGS. 6A-6D illustrate some examples of lesion patterns that may be created with any of the ablation systems described herein.

Figure 6A:
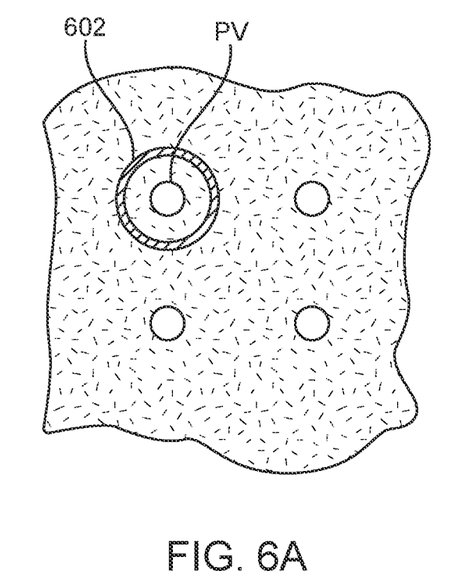
FIGS. 6A-6D illustrate examples of ablation patterns.

FIG. 6A shows a closed loop ablation pattern, here a circular shaped lesion 602 that is disposed around a single pulmonary vein PV. The lesion may be disposed around a right pulmonary vein or a left pulmonary vein. Here the lesion is disposed around a right pulmonary vein. The remaining pulmonary veins do not have a lesion around them.

Figure 6B:
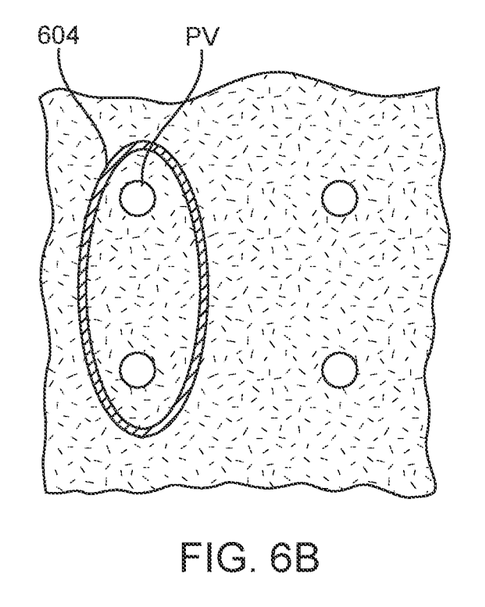

FIG. 6B shows another closed loop, here an elliptical shaped lesion 604 that is disposed around two pulmonary veins PV. The lesion may be disposed around both right pulmonary veins as seen in FIG. 6B, or around both left pulmonary veins.

Figure 6C:
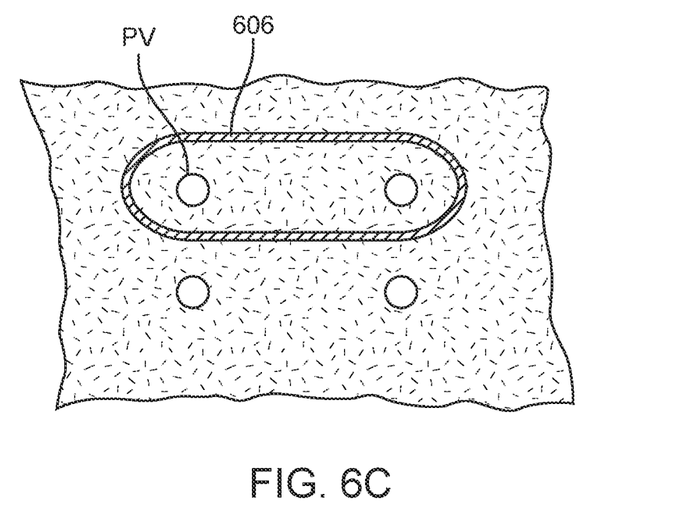

FIG. 6C shows another closed loop, here an elliptical shaped lesion 606 that is disposed around two pulmonary veins PV. The lesion may be disposed around one left pulmonary vein and one right pulmonary vein.

Figure 6D:
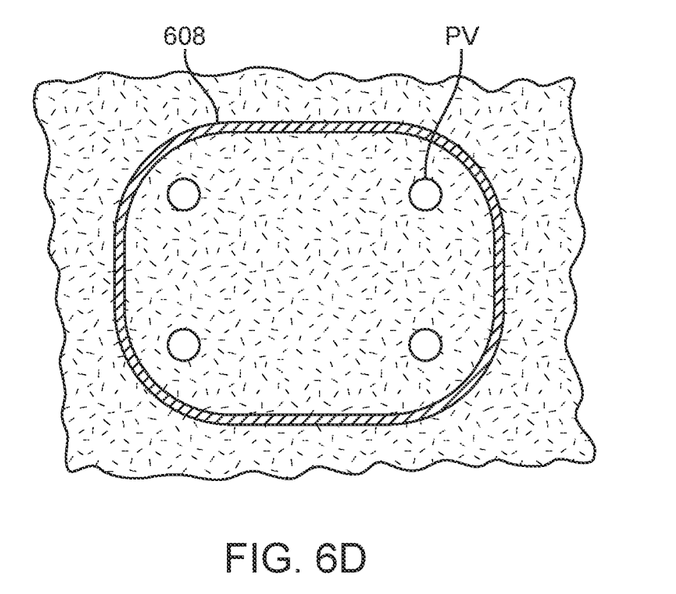

FIG. 6D shows another closed loop, here a circular shaped lesion 608 that is disposed around all four pulmonary veins PV including both right pulmonary veins and both left pulmonary veins.

Any permutation or combination of these patterns is also possible. For example, the closed loop may encircle a superior right pulmonary vein and an inferior left pulmonary vein (not shown), or the closed loop may encircle a superior left pulmonary vein and an inferior right pulmonary vein (not shown). These patterns from diagonal lesion patterns.

Figure 7A:
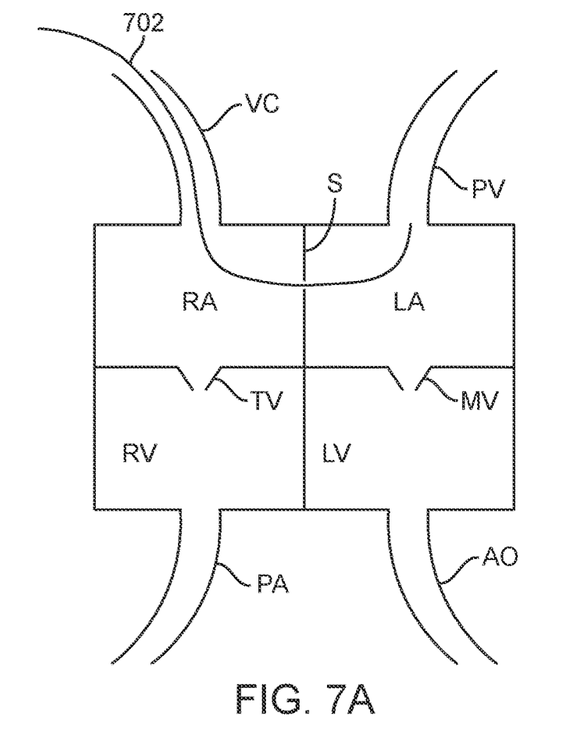
FIG. 7A shows transseptal delivery of the ablation system of FIG. 2.
Figure 7B:
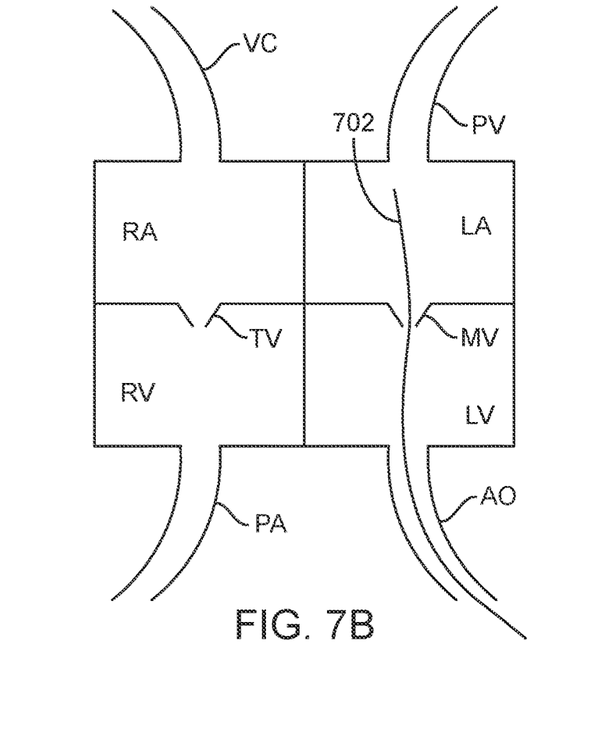
FIG. 7B shows transfemoral delivery of the ablation system of FIG. 2.

FIGS. 7A-7B illustrate examples of delivery of an ablation catheter 702 to the target treatment site. For example, FIG. 7A shows that an ablation catheter 702 which may be any of the ablation catheters optionally with expandable member catheters and optionally with pacing lead or imaging element, may be delivered transseptally from the vena cava VC, into the right atrium RA, across the septal wall S into the left atrium LA where the distal end may be steered toward the target pulmonary vein PV. Transseptal procedures are well known in the art. Other aspects of the anatomy are generally the same as previously discussed with reference to FIG. 1 above.

FIG. 7B shows another delivery route to the target treatment site. Here, the ablation catheter 702 which may be any of the ablation catheters disclosed herein optionally with any expandable member catheter and optionally with pacing wire or imaging element disclosed herein, may be delivered transfemorally in a retrograde direction into the aorta AO, then into the left ventricle LV, across the mitral valve MV into the left atrium LA where the distal end maybe steered toward the target pulmonary vein PV. Other aspects of the heart anatomy are generally the same as previously described above in FIG. 1.

The ablation catheter and system in FIGS. 7A-7B may be any of the ablation catheters and systems disclosed herein optionally with any of the pacing wires or imaging elements disclosed herein.

NOTES AND EXAMPLES

The following, non-limiting examples, detail certain aspects of the present subject matter to solve the challenges and provide the benefits discussed herein, among others.

Example 1 is a system for ablating target tissue, the system comprising: an elongate anchor shaft having a proximal portion, a distal portion, and a lumen extending therebetween; a radially expandable member coupled to the distal portion of the elongate anchor shaft, wherein the radially expandable member has a collapsed configuration for delivery and an expanded configuration for engagement with the target tissue, and wherein in the expanded configuration the radially expandable member is configured to contact the target tissue to provide anchoring thereof and to facilitate visualization of the target tissue; an elongate ablation shaft having a proximal portion, a distal portion, a lumen extending therebetween, wherein the elongate ablation shaft is slidably disposed in the lumen of the elongate anchor shaft, and wherein the distal portion of the elongate ablation shaft is steerable; and an energy source coupled to the distal portion of the elongate ablation shaft, the energy source configured to deliver energy to the target tissue and ablate the target tissue, and wherein actuation of the distal portion of the elongate ablation shaft directs the energy to the target tissue to form a desired ablation path in the target tissue.

Example 2 is the system of Example 1, further comprising a plurality of pull wires disposed in the elongate ablation shaft and coupled to the distal portion of the elongate ablation shaft, wherein actuation of one or more of the plurality of pull wires steers the distal portion of the elongate ablation shaft.

Example 3 is the system of any of Examples 1-2, wherein the plurality of pull wires comprise four pull wires disposed substantially evenly around a circumference of the elongate ablation shaft.

Example 4 is the system of any of Examples 1-3, wherein the plurality of pull wires are disposed in one or more lumens disposed in a wall of the elongate ablation shaft.

Example 5 is the system of any of Examples 1-4, wherein at least one of the plurality of pull wires comprising a first free end, a second free end, and an intermediate portion therebetween, wherein the first free is disposed adjacent a proximal end of the ablation shaft, the intermediate portion extends along the ablation shaft, across a distal portion of the ablation shaft, and returns along the ablation shaft so that the second free end is disposed adjacent the proximal end of the ablation shaft.

Example 6 is the system of any of Examples 1-5, wherein the energy source comprises an ultrasound transducer configured to emit ultrasound energy therefrom.

Example 7 is the system of any of Examples 1-6, wherein the ultrasound energy is a low intensity collimated beam of ultrasound energy.

Example 8 is the system of any of Examples 1-7, wherein the ultrasound energy is emitted in a distal direction from the ultrasound transducer.

Example 9 is the system of any of Examples 1-8, wherein the ultrasound transducer is a disc with a center hole therethrough, the center hole configurated to allow fluid flow therethrough for cooling of the disc.

Example 10 is the system of any of Examples 1-9, further comprising a header element disposed between the ultrasound transducer and the distal portion of the elongate ablation shaft.

Example 11 is the system of any of Examples 1-10, wherein the energy source remains contact free with the target tissue during the ablation.

Example 12 is the system of any of Examples 1-11, wherein the target tissue comprises a pulmonary vein or tissue adjacent thereto.

Example 13 is the system of any of Examples 1-12, wherein actuation of the distal portion of the elongate ablation shaft in a substantially circular motion is configured to steer the distal portion of the elongate ablation shaft in a substantially circular motion to form a closed loop ablation path in the target tissue.

Example 14 is the system of any of Examples 1-13, wherein the ablation path comprises a transmural lesion in the target tissue.

Example 15 is the system of any of Examples 1-14, wherein the radially expandable member comprises a balloon.

Example 16 is the system of any of Examples 1-15, further comprising saline or another optically transparent fluid disposed in the radially expandable member, the saline or another fluid configured to radially expand the radially expandable member.

Example 17 is the system of any of Examples 1-16, wherein the radially expandable member comprises a nipple on a distal end thereof, the nipple configured to be disposed in a lumen of a blood vessel, and wherein the nipple allows fluid to bleed out of the expandable member.

Example 18 is the system of any of Examples 1-17, further comprising an imaging device disposed at least partially in the radially expandable member, wherein the imaging device is configured to provide an image of the ablation path.

Example 19 is the system of any of Examples 1-18, wherein the imaging device comprises a fiber optic imaging device.

Example 20 is the system of any of Examples 1-19, wherein the imaging device is slidably disposed in the elongate ablation shaft lumen.

Example 21 is the system of any of Examples 1-20, further comprising a pacing lead extending distally of the radially expandable member, the pacing lead configured to engage tissue and electrically stimulate the tissue.

Example 22 is the system of any of Examples 1-21, wherein the pacing lead passes through the radially expandable member and the elongate ablation shaft.

Example 23 is the system of any of Examples 1-22, wherein the pacing lead comprises a radially expandable loop on a distal end thereof, the radially expandable loop configured to engage the tissue.

Example 24 is a method for ablating target tissue in a patient having a heart, the method comprising: advancing a radially expandable member into a pulmonary vein; radially expanding the radially expandable member into engagement with the pulmonary vein and anchoring the radially expandable member thereto; positioning an ablation catheter disposed in the radially expandable member so that an energy source on the ablation catheter is disposed adjacent the target tissue; delivering energy from the energy source to the target tissue and ablating the target tissue; and steering a distal portion of the ablation catheter to move the energy source around the pulmonary vein thereby forming a closed loop ablation path.

Example 25 is the method of Example 24, wherein steering the distal portion comprises actuating one or more pull wires coupled to a distal portion of the ablation catheter.

Example 26 is the method of any of Examples 24-25, wherein delivering the energy comprises delivering ultrasound energy from an ultrasound transducer to the target tissue.

Example 27 is the method of any of Examples 24-26, wherein delivering the ultrasound energy comprises delivering a low intensity collimated beam of ultrasound energy.

Example 28 is the method of any of Examples 24-27, wherein delivering the ultrasound energy comprises emitting the ultrasound energy in a distal direction from the ultrasound transducer.

Example 29 is the method of any of Examples 24-28, wherein delivering the energy comprises delivering the energy without contacting the source of energy with the target tissue.

Example 30 is the method of any of Examples 24-29, wherein ablating the tissue comprises transmurally ablating the tissue.

Example 31 is the method of any of Examples 24-30, wherein radially expanding the radially expandable member comprises inflating a balloon.

Example 32 is the method of any of Examples 24-31, wherein advancing the radially expandable member into the pulmonary vein comprises disposing a nipple on a distal end of the radially expandable member into the pulmonary vein.

Example 33 is the method of any of Examples 24-32, further comprising viewing the ablation path with an imaging device.

Example 34 is the method of any of Examples 24-33, further comprising disposing a pacing lead into the pulmonary vein; pacing the pulmonary vein; and monitoring the patient's heart to determine if the pacing is blocked.

In Example 35, the apparatuses, systems or methods of any one or any combination of Examples 1-34 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A system for ablating target tissue, the system comprising:
   an elongate anchor shaft having a proximal portion a distal portion, and a lumen extending therebetween;
   a radially expandable member coupled to the distal portion of the elongate anchor shaft, wherein the radially expandable member has a collapsed configuration for delivery and an expanded configuration for engagement with the target tissue, and wherein in the expanded configuration the radially expandable member is configured to contact the target tissue to provide anchoring thereof and to facilitate visualization of the target tissue;
   an elongate ablation shaft having a proximal portion, a distal portion, and a lumen extending therebetween, wherein the elongate ablation shaft is slidably disposed in the lumen of the elongate anchor shaft, and
   wherein the distal portion of the elongate ablation shaft is steerable; and
   an energy source coupled to the distal portion of the elongate ablation shaft, the energy source configured to deliver energy to the target tissue and ablate the target tissue,
   wherein the energy source comprises an ultrasound transducer configured to emit ultrasound energy therefrom,
   wherein the ultrasound transducer is a disc with a center hole therethrough, the center hole configured to allow fluid flow therethrough for cooling of the disc, and
   wherein actuation of the distal portion of the elongate ablation shaft directs the energy to the target tissue to form a desired ablation path in the target tissue.

2. The system of claim 1, further comprising a plurality of pull wires disposed in the elongate ablation shaft and coupled to the distal portion of the elongate ablation shaft, wherein actuation of one or more of the plurality of pull wires steers the distal portion of the elongate ablation shaft.

3. The system of claim 2, wherein the plurality of pull wires comprise four pull wires disposed substantially evenly around a circumference of the elongate ablation shaft.

4. The system of claim 2, wherein the plurality of pull wires are disposed in one or more lumens disposed in a wall of the elongate ablation shaft.

5. The system of claim 2, wherein at least one of the plurality of pull wires comprises a first free end, a second free end, and an intermediate portion therebetween, wherein the first free end is disposed adjacent a proximal end of the ablation shaft, the intermediate portion extends along the ablation shaft, across a distal portion of the ablation shaft, and returns along the ablation shaft so that the second free end is disposed adjacent the proximal end of the ablation shaft.

6. The system of claim 1, wherein the ultrasound energy is a low intensity collimated beam of ultrasound energy.

7. The system of claim 1, wherein the ultrasound energy is emitted in a distal direction from the ultrasound transducer.

8. The system of claim 1, further comprising a header element disposed between the ultrasound transducer and the distal portion of the elongate ablation shaft.

9. The system of claim 1, wherein the energy source remains contact free with the target tissue during the ablation.

10. The system of claim 1, wherein the target tissue comprises a pulmonary vein or tissue adjacent thereto.

11. The system of claim 1, wherein actuation of the distal portion of the elongate ablation shaft in a substantially circular motion is configured to steer the distal portion of the elongate ablation shaft in a substantially circular motion to form a closed loop ablation path in the target tissue.

12. The system of claim 1, wherein the ablation path comprises a transmural lesion in the target tissue.

13. The system of claim 1, wherein the radially expandable member comprises a balloon.

14. The system of claim 1, further comprising saline or another optically transparent fluid disposed in the radially expandable member, the saline or another fluid configured to radially expand the radially expandable member.

15. The system of claim 1, wherein the radially expandable member comprises a nipple on a distal end thereof, the nipple configured to be disposed in a lumen of a blood vessel, and wherein the nipple allows fluid to bleed out of the expandable member.

16. The system of claim 1, further comprising an imaging device disposed at least partially in the radially expandable member, wherein the imaging device is configured to provide an image of the ablation path.

17. The system of claim 16, wherein the imaging device comprises a fiber optic imaging device.

18. The system of claim 16, wherein the imaging device is slidably disposed in the elongate ablation shaft lumen.

19. The system of claim 1, the system further comprising a pacing lead extending distally of the radially expandable member, the pacing lead configured to engage tissue and electrically stimulate the tissue.

20. The system of claim 19, wherein the pacing lead passes through the radially expandable member and the elongate ablation shaft.

21. The system of claim 19, wherein the pacing lead comprises a radially expandable loop on a distal end thereof, the radially expandable loop configured to engage the tissue.

22. A system for ablating target tissue, the system comprising:
an elongate anchor shaft having a proximal portion a distal portion, and a lumen extending therebetween;
a radially expandable member coupled to the distal portion of the elongate anchor shaft, wherein the radially expandable member has a collapsed configuration for delivery and an expanded configuration for engagement with the target tissue, and wherein in the expanded configuration the radially expandable member is configured to contact the target tissue to provide anchoring thereof and to facilitate visualization of the target tissue;
an elongate ablation shaft having a proximal portion, a distal portion, and a lumen extending therebetween, wherein the elongate ablation shaft is slidably disposed in the lumen of the elongate anchor shaft, and
wherein the distal portion of the elongate ablation shaft is steerable;
an energy source coupled to the distal portion of the elongate ablation shaft, the energy source configured to deliver energy to the target tissue and ablate the target tissue, wherein the energy source comprises an ultrasound transducer configured to emit ultrasound energy therefrom, and
wherein actuation of the distal portion of the elongate ablation shaft directs the energy to the target tissue to form a desired ablation path in the target tissue; and
a header element disposed between the ultrasound transducer and the distal portion of the elongate ablation shaft.

23. A system for ablating target tissue, the system comprising:
an elongate anchor shaft having a proximal portion a distal portion, and a lumen extending therebetween;
a radially expandable member coupled to the distal portion of the elongate anchor shaft, wherein the radially expandable member has a collapsed configuration for delivery and an expanded configuration for engagement with the target tissue, and wherein in the expanded configuration the radially expandable member is configured to contact the target tissue to provide anchoring thereof and to facilitate visualization of the target tissue;
an elongate ablation shaft having a proximal portion, a distal portion, and a lumen extending therebetween, wherein the elongate ablation shaft is slidably disposed in the lumen of the elongate anchor shaft, and
wherein the distal portion of the elongate ablation shaft is steerable;
an energy source coupled to the distal portion of the elongate ablation shaft, the energy source configured to deliver energy to the target tissue and ablate the target tissue, and
wherein actuation of the distal portion of the elongate ablation shaft directs the energy to the target tissue to form a desired ablation path in the target tissue; and
a plurality of pull wires disposed in the elongate ablation shaft and coupled to the distal portion of the elongate ablation shaft, wherein actuation of one or more of the plurality of pull wires steers the distal portion of the elongate ablation shaft,
wherein at least one of the plurality of pull wires comprises a first free end, a second free end, and an intermediate portion therebetween, wherein the first free is disposed adjacent a proximal end of the ablation shaft, the intermediate portion extends along the ablation shaft, across a distal portion of the ablation shaft, and returns along the ablation shaft so that the second free end is disposed adjacent the proximal end of the ablation shaft.

* * * * *